United States Patent
Ziauddin et al.

(10) Patent No.: US 6,668,922 B2
(45) Date of Patent: Dec. 30, 2003

(54) METHOD OF OPTIMIZING THE DESIGN, STIMULATION AND EVALUATION OF MATRIX TREATMENT IN A RESERVOIR

(75) Inventors: Murtaza Ziauddin, Richmond, TX (US); Joel Robert, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 22 days.

(21) Appl. No.: 10/075,207

(22) Filed: Feb. 14, 2002

(65) Prior Publication Data

US 2002/0153137 A1 Oct. 24, 2002

Related U.S. Application Data

(60) Provisional application No. 60/269,656, filed on Feb. 16, 2001.

(51) Int. Cl.[7] .............................................. E21B 43/26
(52) U.S. Cl. ........................ 166/250.05; 166/250.02; 166/307
(58) Field of Search ................... 166/250.02, 250.05, 166/250.07, 304, 307, 282; 73/152.07, 152.11

(56) References Cited

U.S. PATENT DOCUMENTS

| | | | | |
|---|---|---|---|---|
| 5,431,227 A | * | 7/1995 | Montgomery et al. | 166/307 |
| 5,458,192 A | * | 10/1995 | Hunt | 166/250.1 |
| 6,196,318 B1 | * | 3/2001 | Gong et al. | 166/308 |

OTHER PUBLICATIONS

Xiong, Hongjle, *Prediction Of Effective Acid Penetration And Acid Volume For Matrix Acidizing Treatment In Naturally Fractured Carbonates*, SPE Paper 25410 presented at the Production Operations Symposium held in Oklahoma City, OK Mar. 21–23, 1993.

Chen, Yueting, et al., *Reaction–Transport Simulation Of Matrix Acidizing And Optimal Acidizing Strategies*, SPE 37282 presented at the SPE International Symposium on Oilfield Chemistry held in Houston, Texas, Feb. 18–21, 1997.

Huang, T. et al., *Reaction Tate and Fluid Loss: The Keys To Wormhole Initiation and Propagation In Carbonate Acidizing*, SPE Paper 37312 presented at the SPE International Symposium on Oilfield Chemistry held in Houston, Texas, Feb. 18–21, 1997.

Fan, Yong et al., *A Comprehensive Model Of Matrix Acidization*, SPE 38169 presented at the 1997 SPE European Formation Damage Conference held in The Hague, The Netherlands, Jun. 2–3, 1997.

(List continued on next page.)

Primary Examiner—William Neuder
(74) Attorney, Agent, or Firm—Catherine Menes; Brigitte Jeffery; John J. Ryberg (57) ABSTRACT

A method for designing acid treatments provides for the selection of optimal treatment for well stimulation wherein reservoir characteristics are obtained to further select the reaction kinetic data on the minerals of interests, the treatment to the reservoir is scaled up using a mathematical model and real time damage are computed based on bottomhole pressure and injection rate and compared to that predicted by the mathematical model to adjust the treatment. The model generated facilitates optimization of matrix treatments by providing a rapid quantitative evaluation of various treatment strategies for a formation. Stimulation with non-traditional fluid recipes containing mixtures of inorganic and organic acids, and chelating agents can be readily computed. The computed values can then be used in an economic model to justify the additional costs associated with the use of the non-traditional fluids. Apart from optimizing matrix treatments, the method can be used as a development tool for new fluid systems, as a tool for prediction and removal of inorganic scale and for fluid compatibility testing such as that required in water flooding projects.

23 Claims, 4 Drawing Sheets

OTHER PUBLICATIONS

Quinn, M. Anthony, et al., *Designing Effective Sandstone Acidizing Treatments Through Geochemical Modeling*, SPE 38173 presented at the 1997 SPE European Formation Damage Conference held in The Hague, The Netherlands, Jun. 2–3, 1997.

Li, Ying–Hsiao, et al., *Mathematical Modeling of Secondary Precipitation From Sandstone Acidizing*, SPE 39420 presented at the 1998 SPE International Symposium on Formation Damage Control held in Lafayette, Louisiana, Feb. 18–19, 1998.

Gong, M., et al., *Quantitative Model Of Wormholing Process In Carbonate Acidizing*, SPE 52165 presented at the 1999 SPE Mid–Continent Operations Symposium held in Oklahoma City, OK Mar. 28–31, 1999.

Fredd, C.N., *Dynamic Model Of Wormholing Formation Demonstrates Conditions For Effective Skin Reduction During Carbonate Matrix Acidizing* presented at the 2000 SPE Permian Basin Oil and Gas Recovery Conference held in Midland, Texas Mar. 21–23, 2000.

Labrid, J.C., *Thermodynamic and Kinetic Aspects of Argillaceous Sandstone Acidizing*, Society Of Petroleum Engineers, presented at SPE–AIME $49^{th}$ Annual Fall Meeting held in Houston Oct. 6–9, 1974.

Quinn, M.A., *Designing Effective Sandstone Acidizing Treatments Through Geochemical Modeling*, SPE Paper 60846 presented at the 1997 SPE European Formation Damage Control conference held in The Hague Jun. 2–3.

Gdanski, R.D. *Advanced Sandstone–Acidizing Designs With Improved Radial Models*, SPE Paper 52397 first presented at the 1997 SPE Annual Technical Conference and Exhibition held in San Antonio, Texas Oct. 5–6.

* cited by examiner

METHOD OF OPTIMIZING THE DESIGN, STIMULATION AND EVALUATION OF MATRIX TREATMENT IN A RESERVOIR

This patent application is a non-provisional application of provisional application Ser. No. 60/269,656 filed Feb. 16, 2001.

BACKGROUND OF THE INVENTION

1. Field of the Invention

The present invention is generally related to hydrocarbon well stimulation, and is more particularly directed to a method for designing matrix treatment, or generally any treatment with a fluid that will react with the reservoir minerals or with chemicals resulting for instance from a previous treatment. The invention is particularly useful for designing acid treatment such as for instance mud acid treatments in sandstone reservoirs.

2. Discussion of the Prior Art

Matrix acidizing is among the oldest well stimulation techniques. It is applied to sandstone formations to remove near-wellbore damage, which may have been caused by drilling, completion, production, or workover operations. Matrix acidizing is accomplished by injecting a mixture of aids (typically hydrofluoric and hydrochloric acids) to dissolve materials that impair well production, as a rule designated as near-wellbore damages.

Matrix treatments ma sandstone reservoirs have evolved considerably since the first mud acid treatment in the 1930s. Treatment fluid recipes have become increasingly complex. Several additives are now routinely used and organic acids are frequently used in high temperature formations to avoid precipitation reactions. Chelating agents are often added to avoid precipitation in formations with high carbonate content.

Substantial production improvements can be achieved by this type of well stimulation technique if treatments are engineered properly. However, matrix treatments are also often a main contributor to reservoir damages. Indeed, the side reactions that occur in almost all mud acid treatments, lead to the formation of precipitates. Precipitates plug pore spaces and reduce permeability and can therefore adversely affect acid treatments if precipitates deposit near the wellbore. Far from the well precipitates are considered to have negligible effect. Moreover, recent studies have made the industry wary of damage due to secondary and tertiary reactions. Accurate prediction of the effectiveness of a matrix treatment involves calculation of the rates of the dissolution and re-precipitation reactions of minerals because the rates dictate where precipitates will be deposited in the reservoir.

Moreover, sandstone mineralogy is quite complex and acid/mineral compatibility as well as acid/crude oil compatibility is often an issue. At present, there is a lack of tools that can predict accurately the reactivity of acids with clays, and consequently, there are treatments currently in practice that use empirical rules—or at the opposite extreme, rely on extensive costly and time-consuming laboratory testing.

Beyond the treatment fluid selection, the pumping schedule is also a crucial parameter. In The *Stimulation Treatment Pressure Record-An Overlooked Formation Evaluation Tool,* by H. O. McLeod and A. W. Coulter, JPT, 1969, p. 952–960, a technique is described wherein each injection stage or shut-in during the treatment is considered as a short individual well test. The transient reservoir pressure response to the injection of fluids is analyzed and interpreted to determine the conditions of the wellbore skin and formation transmissibility.

In *New Method Proves Value of Stimulation Planning,* Oil & Gas Journal, V 77, NO 47, PP 154–160, Nov. 19, 1979, G. Paccaloni proposes a method based on the instantaneous pressure and injection rate values to compute the skin factor at any given time during the treatment. Comparison is made with standard curves calculated for fixed values of skin effect to evaluate skin effect evolution during treatment. Standard curves are generated using Darcy's equations for steady state, single phase and radial horizontal flow in reservoirs.

A technique presented by Prouvost and Economides enables continuous calculation of the skin effect factor during the course of the treatment and accounts for transient response, see *Real-time Evaluation of Matrix Acidizing,* Pet. Sci, and Eng., 1987, p.145–154, and *Applications of Real-time Matrix Acidizing Evaluation Method,* SPE 17156, SPE Production Engineering, 1987, 4, No. 6, 401–407. This technique is based on a continuous comparison of the measured and presumed good reservoir description including the type of model and well and reservoir variables of the subject well.

It is also known from U.S. Pat. No. 5,431,227 to provide a method for matrix stimulation field monitoring, optimization and post-job evaluation of matrix treatments based on calculated and measured bottom hole pressure used in a step rate test to estimate the damage skin.

A number of sandstone acidizing models have been presented in the literature aiming at computing changes in porosity resulting from the dissolution and precipitation of minerals.

In the lumped mineral models, the complex sandstone mineralogy is lumped into characteristic minerals and an average reaction rate for these minerals is determined from core tests. In two mineral models the sandstone minerals are lumped into fast- and slow-reacting groups on the basis of their reactivity with HF. Two mineral models do not account for precipitation reactions. A three mineral lumped model has also been proposed in S. L. Bryant, SPE 22855, An Improved Model of Mud Acid/Sandstone Acidizing, in SPE Annual Technical Conference and Exhibition, 1991, Dallas. The third mineral accounts for the precipitation of amorphous silica. Disadvantages of lumped mineral models are that they do not allow for equilibrium reactions to be modeled and need to be carefully calibrated to the treatment condition and formation of interest. Therefore, these models are not applicable to fluids systems containing weak acids (e.g. most organic acids) and chelating agents and are not reliable outside the calibrated region.

The equilibrium approximation is another approximation that is frequently used for the design of matrix treatments. This model has been presented in Walsh, M. P., L. W. Lake, and R. S. Schechter, SPE 10625, A Description of Chemical Precipitation Mechanisms and Their Role in Formation Damage During Stimulation by Hydrofluoric Acid, in SPE International Symposium on Oilfield and Geothermal Chemistry, 1982, Dallas. In the equilibrium approximation it is assumed that the reactions are much faster than the contact time of the minerals with the acids. The equilibrium constants for the reactions are usually better known than the rate constants, so large reaction sets can be included and complex sandstone mineralogy can be accounted for without speculating on the reactions and rate laws as is necessary in the lumped mineral approach. Unfortunately, the assumption that the reactions are much faster than the contact time is not valid for the injection rates used in most acid treatments and thus the equilibrium approach is useful only as an indicator for precipitation. The question that must be answered for a successful design is not if but where precipitation will occur. An equilibrium model alone with no time dependence cannot answer this question.

To address this discrepancy in the equilibrium models, partial local equilibrium models have been proposed and first described in Sevougian, S. D., L. W. Lake, and R. S. Schechter, KGEOFLOW: A New Reactive Transport Simulator for Sandstone Matrix Acidizing, SPE Production & Facilities, 1995: p. 13–19 and in Li, Y., J. D. Fambrough, and C. T. Montgomery, SPE 39420, Mathematical Modeling of Secondary Precipitation from Sandstone Acidizing, SPE International Symposium on Formation Damage Control, 1998, Lafayette. The partial equilibrium approach combines the kinetic and equilibrium approaches. Slow reactions are modeled with a kinetic model, and an equilibrium model is used for fast reactions. This computation scheme enables comprehensive and flexible modeling of sandstone acidizing, but traditionally suffered from several disadvantages. First, accurate computation of the activity coefficients for high acidic and high ionic strength solutions is difficult. Second, due to inefficient numerical algorithms numerical convergence was a frequent problem. Therefore, only 1–2 precipitated mineral species could be practically simulated. Third, only a limited thermodynamic data was available. Hence, simulations for hot reservoirs and with nontraditional fluid systems were not possible.

The previous models are applicable to a limited range of temperatures, injection rates and mineral composition. So yet, despite the important risk of damaging a reservoir, no satisfactory method for modeling matrix treatments over a much broader range of these variables, to make the model more reliable for extrapolating laboratory data to field conditions.

This failure of the existing models is all the more critical that treatment fluid recipes have become increasingly complex. Several additives are now routinely added, organic acids are frequently used in high temperature formations to avoid precipitation reactions and chelating agents are often added to avoid precipitation in formations with high carbonate content.

SUMMARY OF THE INVENTION

The subject invention is directed to a method for designing matrix treatments, and more particularly, for stimulation with reactive fluid in sandstone formations, even though the invention extends to other areas such as carbonate acidizing, scale inhibition and related fields. In particular, according to a first embodiment, the invention relates to a method for selecting the optimal treatment wherein reservoir characteristics including reservoir minerals are obtained and a treatment fluid comprising a mixture of chemical species is designed to further select a subset of chemical reactions that can occur between the reservoir minerals and the treatment fluid the reaction kinetic and equilibrium data on the minerals and chemical species of interests, and depending on the predicted damages consecutive to those reactions, the stimulation treatment is adjusted to optimize the results. In other words, the invention proposes a virtual chemical laboratory that makes it possible to simulate a large number of laboratory tests.

In a second embodiment of the invention, the method further includes modeling a reservoir core having a length, a diameter and a permeability so that the invention makes it possible to simulate core tests. The invention also provides a way to simulate sequential treatments where successions of treatment fluids are injected at specific rates.

In a third embodiment of the invention, the method further includes scaling up the treatment to a reservoir using a mathematical model to predict damages resulting from the treatment. In a most preferred embodiment, the invention includes selecting a treatment, carrying out the treatment on a well while real time damage are computed based on bottomhole pressure and injection rate and simultaneously, performing a simulation scaled up to the reservoir to compare the predicted damages and the computed damages and adjusting the treatment if required.

In the preferred embodiments of the invention, the three flow geometries have been implemented: (1) batch, (2) core and (3) reservoir geometries. The batch flow geometry approximates the reactions occurring in a flask or a beaker, the core flow geometry approximates linear flow in cores such as that in laboratory core flooding experiments, and the reservoir flow geometry approximates flow in a single layer, radially symmetric reservoir. The batch and core flow geometries provide a means for validating the mathematical model, so that the predictions for the reservoir can be made with more confidence.

The model generated by the method of the subject invention can facilitate optimization of matrix treatments by providing a rapid quantitative evaluation of various treatment strategies for a formation. Stimulation with non-traditional fluid recipes containing mixtures of inorganic and organic acids, and chelating agents can be readily computed. The computed values can then be used in an economic model to justify the additional costs associated with the use of the non-traditional fluids. Apart from optimizing matrix treatments, the method of the subject invention can also be used as a development tool for new fluid systems, as a tool for prediction and removal of inorganic scale and for fluid compatibility testing such as that required in waterflooding projects.

The method of the subject invention combines a geochemical simulator to an extensive database of thermodynamic properties of aqueous chemical species and minerals. The subject invention overcomes many limitations of previous simulators. Chemical equilibrium calculations can be performed between any number of minerals and aqueous solutions, whereas previous simulators were limited to only one or two precipitated minerals. Additionally, any number of kinetically controlled reactions can be simulated with user-defined kinetics.

The modeling method of the subject invention is a finite-difference geochemical simulator capable of modeling kinetic and/or equilibrium controlled reactions in various flow geometries. The mathematical formulation provides the capability to model an arbitrary combination of equilibrium and kinetic reactions involving an arbitrary combination of equilibrium and kinetic reactions involving an arbitrary number of chemical species. This flexibility allows the simulation model to act as a pure kinetic model if no equilibrium are specified or as a pure equilibrium model if both kinetic and equilibrium reactions are specified. A semi-implicit numerical scheme is used for integration in time for kinetic reactions. This scheme provides greater numerical stability compared to explicit schemes, especially at high temperature. A Gibbs free energy minimization algorithm with optimized stoichiometry is used in computing chemical equilibrium between aqueous species and minerals. Base specie switching is implemented to improve convergence. The resulting algorithm for chemical equilibrium calculation is of greater numerical stability and is more efficient than prior art algorithms based on a non-stoichiometric approach.

The treatment design preferably includes variables such as fluid type, composition, volume, pumping sequence and injection rates. A database is used to get the reaction kinetics data. If insufficient data is available, laboratory experiments may be conducted, preferably using multiple linear core flow tests for a range of injection rates.

The reservoir characteristics typically include mineralogy data, permeability and preferably, an estimate of the quantity and depth of damage such as scales, fines migration or drilling-related damages including the initial damage skin. This estimate can be made for instance based on nodal analysis or available mud and resistivity logs. The reservoir characteristics may be stored in a database and if not already available, are obtained by geochemical logging or from core analysis and further stored in the database for further use.

The model is preferably calibrated with data including effluent analysis and permeability evolution (including predicted damages). Sensitivity analysis may be also performed to optimize the design variables and select improved treatment design.

Once an optimized design has been selected, the execution of the treatment can begin and damage skin can be computed on a real time basis. This allows a comparison with the predicted damages and, if appropriate, adjustment of the treatment.

Specifically, the invention comprises data collection, design optimization, execution and evaluation. In the execution phase, the damage is computed in real time from either calculated or measured values of bottomhole pressure and injection rate. It can then be compared to the computed damage skin with that predicted by the mathematical model. The model can thereafter be refined by better estimates for type, quantity and depth of damage to match the measured values and, if needed, appropriate changes to the treatment design are performed.

Post treatment data, such as flowback analysis, production data and production logs, are used to further refine the mathematical model and the estimates of damage depth and quantity. The treatment data can finally be uploaded into the database so it can be used in improving future treatment designs.

The method of the subject invention facilitates treatment design with the methodology described above. This can be implemented with a mathematical model and databases. The mathematical model may comprise the following components:

1. Algorithm for automatic selection of the various applicable chemical reactions for the defined system of fluids and minerals
2. Modeling of organic acids and chelating agent chemistry for sandstone acidizing
3. Algorithm for scale up from core to reservoir
4. Modeling of multiple precipitates The mathematical model can be extended later to other processes such as carbonate acidizing, scale inhibition, or other mechanisms that involve fluid/reservoir interaction.

According to a preferred embodiment, the method of the subject invention incorporates extensive databases of minerals, chemical reactions, fluids and reservoirs in order to feed the mathematical model with accurate geological, physical and reactivity data, thereby ensuring the success of the process. Users preferably have the ability to create new components (fluids, minerals, reactions) and add them to the database for future use. This allows continued expansion of the methodology of the subject invention to new systems and new processes. In accordance with the teachings of the subject invention, chemical equilibrium calculations can be performed between any number of minerals and aqueous solutions.

In the preferred embodiment of the invention, the essential steps are stored on a CD-ROM device. In another preferred embodiment, the method/process is downloadable from a network server, or an internet web page. Moreover, the present invention can be subsumed using a software developed to assist acid treatments.

BRIEF DESCRIPTION OF THE DRAWINGS

FIG. 1 shows a comparison of the measured effluent concentration of HF, Al, and Si with those predicted by the model of the present invention.

FIG. 2 are graphs providing a snapshot of the reservoir at the end of the mud acid stage.

FIG. 3 compares the results for different injection rates and a different mud acid formulation.

FIG. 4 shows the result of the treatment if the reservoir had been damaged with a mineral similar to kaolinite.

DETAILED DESCRIPTION OF THE PREFERRED EMBODIMENTS

The methods of the subject invention provide a virtual laboratory geochemical simulator for well simulating by permitting and supporting scaled laboratory modeling to be scaled to reservoir adaptability. The laboratory experiments validate the model and permit scaling up to reservoir level with precision and efficiency. The fundamental tools provide: (1) a reaction model, (2) analysis of the model, (3) testing at the model level, (4) validation, and (5) scale-up to reservoir. This permits laboratory review and modeling of formation damage with predictabilaty, accurate confirmation and ready and efficient adjustability. Specifically, the methods of the subject invention permit laboratory design, execution and evaluation prior to reservoir application greatly increasing the efficiency of the process.

The numerical model of the present invention is a finite-difference geochemical simulator capable of modeling kinetic and/or equilibrium controlled reactions (i.e. partial local equilibrium reaction model) in various flow geometries. The mathematical formulation provides the capability to model an arbitrary combination of equilibrium and kinetic reactions involving an arbitrary number of chemical species. This flexibility in the mathematical formulation allows it to act as a pure kinetic model if no equilibrium reactions are specified, or a pure equilibrium model if no kinetic reactions are specified, or as a partial equilibrium model if both kinetic an equilibrium reactions are specified. A semi-implicit numerical scheme is used for integration in time for kinetic reactions. This scheme provided greater numerical stability compared to explicit schemes, especially at high temperature. A Gibbs free energy minimization algorithm with optimized stoichiometry is used in computing chemical equilibrium between aqueous species and minerals. Base specie switching is preferably implemented to improve convergence. The resulting algorithm for chemical equilibrium calculation was found to be much more numerically stable and computationally efficient than algorithms based on the non-stoichiometric approach.

In this embodiment, three flow geometries are implemented in the simulator. These are batch, core and reservoir flow geometries. The batch flow geometry approximates reactions occurring in a flask or a beaker, the core flow geometry approximates linear flow in cores such as that in laboratory core flooding experiments, and the reservoir flow geometry approximates flow in a single layer, radially symmetric reservoir. The batch and core flow geometries provide a means for validating the mathematical model, so that the predictions for the reservoir can be made we more confidence. For example, the geochemical simulator can be validated with measured effluent ion concentrations and the permeability evolution from laboratory core flow experiments, prior to making predictions for the reservoir.

Typical matrix stimulation fluids are extremely non-ideal. The ideal solution assumption usually breaks down for salt concentrations higher than that of fresh water. Activity coefficients capture deviations from ideal solution behavior, and are therefore crucial for accurate modeling of kinetic and equilibrium reactions in concentrated electrolyte solutions (e.g. matrix treatment fluids containing acids and brines).

The following symbols and their definitions are used throughout this application and the appended claims:

$A_\gamma$=electrostatic Debye-Hückel parameter
$A_{j,s}$=specific reactive surface area of mineral j (m²/kg)
$A_A$, $A_B$, $A_C$, $A_W$=activity of aqueous species A, B, C and water (kgmole/m3)
$a_i$ (P, T), $a_{i,P_rT_r}$=ionic diameter, ionic diameter at reference temperature and pressure (Å)
$a_{i,1-4}$=parameter in Helgeson EOS for aqueous species
$b_i$=salting-out parameter for specie i (kg/mol)
$B_\gamma$=electrostatic Debye-Hückel parameter
$\dot{B}(T)$=deviation function describing the departure of the mean ionic activity coefficient of an electrolyte from that predicted by Debye-Hückel expression (kg/mol)
$b_{NaCl}$=electrostatic salvation parameter for NaCl (kg/J)
$b_{Na+Cl-}$=short-range interaction parameter for NaCl (kg/mol)
$C_{p,i}$=heat capacity of specie i at constant pressure (J/mol-K)
$C_{1-2}$=parameter in variable reaction order kinetic model (1/K)
$c_{i,1-2}$=parameters in Helgeson EOS for aqueous species
$E_a$, $E'_a$=activation energy (J/mol)
$f(T)$=temperature function in variable reaction order kinetic model
$G_{i,P_r,T_r}^\circ G_{i,P_t,T_t}^\circ$=standard molal Gibbs free energy of formation at subscripted temperature and pressure (J/mol)

g(P, T)=pressure and temperature dependent solvent function (Å)
$H_i^\circ$=standard molal enthalpy of formation (J/mol)
I=ionic strength of solution (mol/kg)
K=equilibrium constant
$K"_0$, $k"_0$=pre-exponential factors
$k_0$, k=initial and final permeability (mD)
$M_{j,0}$, $M_j$=initial and final volume fraction of mineral j (m3/m3)
$M_{j,w}$=molecular weight of mineral j (g/mol)
$[M_j]$=concentration of mineral j (kgmol/m³)
$m_i$, $\vec{m}$=molality of specie i and vector of molalities (mol/kg solvent)
P, $P_r$=pressure (bar) and standard pressure (1 bar)
$P_{inj}$=bottomhole injection pressure (bar)
$P_{res}$=reservoir pressure at out boundary (bar)
R=gas constant (=8.314 J/mol-K)
rate=volumetric reaction rate (kg mole mineral/m³ sec)
$S_{i,P_r,T_r}^\circ$=standard molal entropy of formation at $P_r$ and $T_r$ (J/mol-K)
T, $T_r$=temperature (K) and standard temperature (298.15 K)
$V_{P_r,T_r}^\circ$=standard molal volume at $P_r$ and $T_r$ (m³/mol)
x, y, z=reaction order with respect to species A, B and C
$Y_{P_r,T_r}$=electrostatic Born function at $P_r$ and $T_r$
$Z, Z_{P_r,T_r}$=electrostatic Born function at P and T, and at $P_r$ and $T_r$
$z_i$=ionic charge of specie i
$\beta_{i,0-7}$=heat capacity parameter for specie i
$\gamma_i$=activity coefficient for specie i
$\delta_j$=Labrid parameter for mineral j
$\xi_{i,1-5}$=chemical potential parameters for specie i
$\eta$=constant (=694630.393 ÅJ/mol)
$\Theta$=constant (=298 K)
$\theta_{i,1-3}$=Maier-Kelly heat capacity coefficients
$\mu_i, \mu_j^0$=chemical potential and standard chemical potential of specie i (J/mol)
$\mu_w, \mu_w^0$=chemical potential and standard chemical potential of water (J/mol)
$v_i$=stoechiometric coefficient of specie i (positive for products, negative for reactants)
$\phi_0$=initial porosity
$\Psi$=constant (=2600 bars)
$\Omega$=moles of water/kg
$\omega_i, \omega_{i,P_r,T_r}$=Born coefficient of specie i at P and T, and at $P_r$ and $T_r$ (J/mol)

Activity coefficient models available in a typical prior art version of the simulator are shown in Table 1:

TABLE 1

Activity Coefficient Models

Extended Debye-Hückel $$\log \gamma_i = \left( \frac{-z_i^2 A_\gamma \sqrt{I}}{1 + B_\gamma a_i \sqrt{I}} \right) + \Gamma$$

Davies $$\log \gamma_i = -z_i^2 A_\gamma \left( \frac{\sqrt{I}}{1 + \sqrt{I}} - 0.3I \right)$$

B-Dot $$\log \gamma_i = \left( \frac{-z_i^2 A_\gamma \sqrt{I}}{1 + B_\gamma a_i(P, T) \sqrt{I}} \right) + \Gamma + \dot{B}(T)I$$

$$a_i(P, T) = a_{i,Pr,Tr} + 2|z_i|g(P, T)$$

TABLE 1-continued

Activity Coefficient Models

HFK $$\log \gamma_i = \left(\frac{-z_i^2 A_\gamma \sqrt{I}}{1 + B_\gamma a_i(P,T)\sqrt{I}}\right) + \Gamma +$$

$$\left(\frac{2\eta z_i^2}{a_i(P,T)} b_{NaCl} + b_{Na^+Cl^-} - 0.19(|z_i| - 1)\right) I$$

$$a_i(P,T) = a_{i,Pr,Tr} + 2|z_i|g(P,T)$$

Neutral species     $\log \gamma_i = b_i I$

Water $$\log A_w = \frac{1}{\Omega}\left(\frac{-\sum m_i}{\ln 10} + \frac{2}{3}A_\gamma I^{1.5}\sigma - \dot{B}(T)I^2\right)$$

$$\sigma = \frac{3}{(4B_\gamma\sqrt{I})^3}\left(1 + 4B_\gamma\sqrt{I} - \frac{1}{1 + 4B_\gamma\sqrt{I}} - 2\ln(1 + 4B_\gamma\sqrt{I})\right)$$

The Extended Debye-Hückel uses a species dependent ionic size. The Davies model (in Davies, C. W., Ion Association. 1962, London: Butterworths) uses a constant ionic size and requires only the specie charge. The B-Dot model (in Helgeson, H. C., Thermodynamic of Hydrothermal Systems at Elevated Temperatures and Pressures, American Journal of Science, 1969. 267 (Summer): p. 729–804) captures the temperature dependence of activity coefficients. The HKF model is described in Helgeson, H. C., D. H. Kirham, and G. Flowers, Theoretical Prediction of the Thermodynamic Behavior of Aqueous Electrolytes at High Pressures and Temperatures: IV. Calculation of Activity Coefficients, Osmotic Coefficients, and Apparent Molal and Standard and Relative Partial Molal Properties to 600° C. and 5 KB, Amer. J. Sci., 1981. 281: p. 1249–1516. Activity coefficients in this model are computed by specifying the specie charge and ion-size under standard conditions. All other parameters in the equation are computed internally in the simulator. For aqueous species for which ion-size data is not available, an estimate for ion-size from species with similar charge and atomic structure and use of the HKF model gives a reasonable representation for most stimulation.

For neutral species in aqueous solutions the salting out model is used. The value of $b_i$ in this model is typically zero or very close to zero for most species. Therefore for species for which this parameter is not known a value of zero is usually accurate enough for most simulations.

Once the mineralogy and treatment fluids are specified, the system may automatically select the applicable kinetic reactions and presents them to the user for review. The user may then accept the default reactions, add new reactions or modify the kinetics of the default reactions. The standard database provided with the program contains data for common matrix reactions. New reactions may be added by specifying the reaction stoichiometry and kinetic rate law parameters. Table 2 lists kinetic rate laws preferably implemented:

TABLE 2

Reaction Rate Law Models

| Reaction Rate Law | Equation |
| --- | --- |
| Arrhenius Surface | rate = $A_{j,s}M_{j,w}[M_j]k_0"e^{-Ea/RT}$ $A_A^x A_B^y A_C^z$ |
| Catalytic | rate = $A_{j,s}M_{j,w}[M_j]k_0"e^{-Ea/RT}$ $[1 + K_0"e^{-Ea40/RT}A_A^x]A_B^y$ |
| Variable Reaction Order | rate = $A_{j,s}M_{j,w}[M_j]k_0"e^{-Ea/RT}A_A^{f(T)}$ $f(T) = C_1T/(1 - C_2T)$ |

The reaction rate laws are formulated in pseudo-homogeneous form i.e. the heterogeneous (surface) reaction between the aqueous phase and the mineral is multiplied by the factor $A_{j,s}M_{j,w}[M_j]$ to compute a volumetric reaction rate. Any number of kinetic reactions can be specified for a simulation.

As for kinetically controlled reactions, the appropriate aqueous species and minerals, and corresponding thermodynamic data are automatically selected from the database and presented to the user for review, once the mineralogy and treatment fluids are specified. The user may then accept the default selections, add new species or minerals or modify the default properties. A brief description of the calculation procedure is presented below to assist in adding to or modifying thermodynamic data for aqueous species and minerals.

Standard partial molal free energy (standard chemical potential) at simulation temperature and pressure, $\mu_i^0(T, P)$, is required for each chemical specie that must be added to the equilibrium calculation. The value of $\mu_i^0(T, P)$ may be entered directly for each specie, or a model to compute $\mu_i^0(T, P)$ must be selected. Table 3 gives a list of available models for computing:

TABLE 3

Models for Calculating Standard Chemical Potential

| Model | Equation |
|---|---|
| Helgeson EOS (for aqueous species) | $\mu_i^o(T, P) = G_{i,P_r,T_r}^o - S_{i,P_r,T_r}^o(T - T_r) + c_{i,1}\left[T\ln\frac{T}{T_r} - T + T_r\right] -$ $c_{i,2}\left\{\left[\left(\frac{1}{T-\Theta}\right) - \left(\frac{1}{T_r-\Theta}\right)\right]\left[\frac{\Theta-T}{\Theta}\right] - \frac{T}{\Theta^2}\ln\left(\frac{T_r(T-\Theta)}{T(T_r-\Theta)}\right)\right\} +$ $a_{i,1}(P - P_r) + a_{i,2}\ln\left(\frac{\Psi+P}{\Psi+P_r}\right) + \left(\frac{1}{T-\Theta}\right)\left[a_{i,3}(P - P_r) + a_{i,4}\ln\left(\frac{\Psi+P}{\Psi+P_r}\right)\right] -$ $\omega_i(Z + 1) + \omega_{i,P_r,T_r}(Z_{P_r,T_r} + 1) + \omega_{i,P_r,T_r}Y_{P_r,T_r}(T - T_r)$ |
| Helgeson EOS (for minerals) | $\mu_i^o(T, P) = G_{i,P_r,T_r}^o - S_{i,P_r,T_r}^o(T - T_r) + \int_{T_r}^{T}(\theta_{i,1} + \theta_{i,2}T + \theta_{i,3}T^{-2})dT -$ $T\int_{T_r}^{T}(\theta_{i,1} + \theta_{i,2}T + \theta_{i,3}T^{-2})d\ln T + V_{P_r,T_r}^o(P - P_r)$ |
| CpModel (for aqueous species and minerals) | $C_{p,i} = \beta_{i,0} + \beta_{i,1}T^{-0.5} + \beta_{i,2}T^{0.5} + \beta_{i,3}T^{-1} + \beta_{i,4}T + \beta_{i,5}T^{-2} + \beta_{i,6}T^2 + \beta_{i,7}T^{-3}$ $C_{p,i} = \left(\frac{\delta H_i^o}{\delta T}\right)_P, \left(\frac{\delta(\mu_i^o/T)}{\delta T}\right)_P = -\frac{H_i^o}{T^2}$ |
| Polynomial Model (for aqueous species and minerals) | $\mu_i^o(T, P) = G_{i,P,T_r}^o + \xi_{i,1}T + \xi_{i,2}T^2 + \xi_{i,3}T^3 + \xi_{i,4}T^4 + \xi_{i,5}T^5$ |

Helgeson equation of state (EOS) (in Helgeson, H. C., et al., Summary and Critique of the Thermodynamic Properties of Rock-forming Minerals. American Journal of Science, 1978. 278-A: p. 229 and Tanger, J. C. and H. C. Helgeson, Calculation of the Thermodynamic and Transport Properties of Aqueous Species at High Pressures and Temperatures: Revised Equation of State for the Standard Partial Molal Properties of Ions and Electrolytes. Amer. J. Sci, 1988. 288: p. 19–98.) is the preferred model for both aqueous species and minerals, and majority of data provided with the program is in this form. Chemical species for which data is not available in Helgeson EOS form, the CP model or the polynomial model may be used to estimate $\mu_i^o(T, P)$. For chemical species for which data is only available in equilibrium constant form, $\mu_i^o(T, P)$ for the specie can be calculated from the following thermodynamic identity $$\ln(K) = \frac{-\sum v_i \mu_i^o}{RT},$$

provided the values of $\mu_i^o(T, P)$ for all the other chemical species in the reaction are known. In a preferred embodiment of the present invention, a graphical tool can be provided to assist in the conversion of equilibrium constant data to free energy form.

Once $\mu_i^o(T, P)$ for aqueous species i is computed at simulation temperature and pressure, the chemical potential of the aqueous species in solution is then computed internally in the simulator from the following equation $$\mu_i(T, P, \vec{m}) = \mu_i^o(T, P) + RT\ln\gamma_i(T, P, \vec{m})m_i$$

For solvent (water) the following equation is used $$\mu_w(T, P, \vec{m}) = \mu_w^o(T, P) + RT\ln a_w(T, P, \vec{m})$$

For minerals that are equilibrated with the aqueous phase species, a separate pure solid phase for that mineral is assumed (i.e. no solid solutions). The equation for the chemical potential for the solid phase specie than simplifies to $$\mu_s(T, P) = \mu_s^o(T, P)$$

The numerical algorithm then computes the value of $\vec{m}$ for which the system Gibbs free energy is a minimum and the element abundance constraint is satisfied.

The kinetic and equilibrium models described above compute changes in porosity due to dissolution and precision of minerals. A porosity-permeability relation is then needed to compute the permeability and hence the skin for the treatment. Several porosity-permeability models have been proposed in the literature including the Labrid Model (in Labrid, J. C., Thermodynamic and Kinetic Aspects of Argillaceous Sandstone Acidizing. SPEJ, April 1975: p. 117–128). According to the invention, the following modified Labrid is preferably used:

$$\frac{k}{k_o} = \prod_j \left[\frac{\phi_0 + M_{o,j} - M_j}{\phi_0}\right]^{\delta_j}$$

The modified Labrid model allows each mineral to uniquely impact the permeability, whereas in most other models, permeability changes are completely determined by net changes in porosity without accounting for the identities of the dissolved or precipitated minerals. The parameter $\delta_j$ in the modified Labrid model is specific to each mineral and allows the mineral identity to impact the permeability. The higher the value of $\delta_j$ the stronger the impact.

APPLICATION EXAMPLE

The main features of the invention are illustrated in this section by means of a simple application example. The example is based on core test data reported by Hsi et al (IN Hsi, C. D., S. L. Bryant, and R. D. Neira, SPE 25212 Experimental Validation of Sandstone Acidization Models, in SPE International Symposium on Oilfield Chemistry. 1993. New Orleans) for the Endicott Kediktuk sandstone formation in Alaska. The core tests were conducted on damaged cores at 80° C. with 12/3 Mud acid. The length and diameter of the core plugs were 7.6 and 2.54 cm, respectively. An inductively coupled plasma (ICP) spectrophotometer was used to measure effluent Al and Si concentrations. The HF concentration in the effluent was measured gravimetrically using the weight-loss method with pre-weighted glass slides. The mineralogy of the Kekiktut formation is 98% Quartz and 2% kaolinite.

FIG. 1 shows a comparison of the measured effluent concentration of HF, Al, and Si with those predicted by the model of the present invention. The solid lines represent the modeling results, the triangles in FIGS. 1A, 1C and 1E indicate experimental data for the normalized HF concentration (the normalized HF concentration is the ratio of the HF in the effluent to the injected HF concentration. In FIGS. 1B, 1D and 1F, the squares represent the Al concentration and the circles the concentration of Si. The tests were performed at 80° C., with 12-3 mud acid, at a flow rate of 0.033 cm/s (FIGS. 1A and 1B), with 12-3 mud acid and a flow rate of 0.0099 cm/s (FIGS. 1C and 1D) and with 6-1.5 mud acid at a flow rate of 0.0099 cm/s (FIGS. 1E and 1F). The model provides a reasonable match to the experimental data even with an order of magnitude change in the flow rate. The match with experimental data was obtained using the default selections of kinetic and thermodynamic data. The match can further be improved by fine tuning the default values.

Figure 1A:
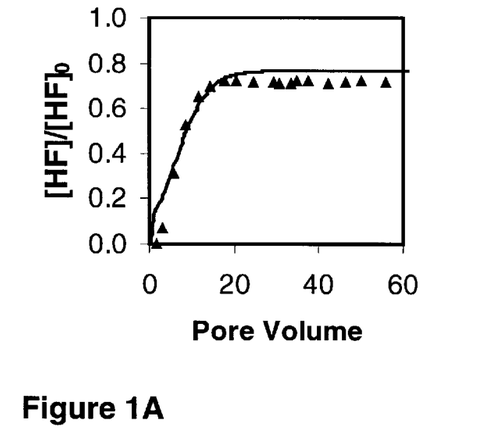
Figure 1B:
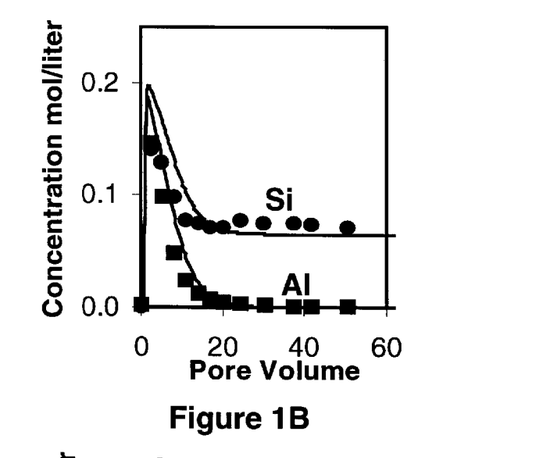
Figure 1C:
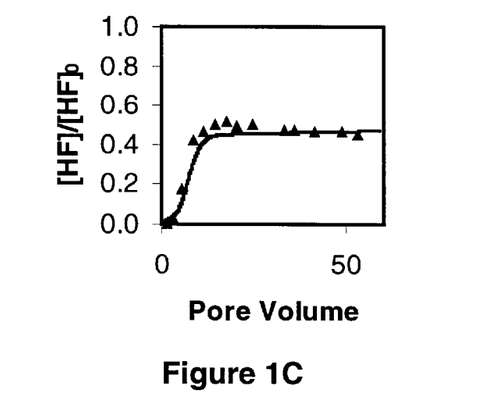
Figure 1D:
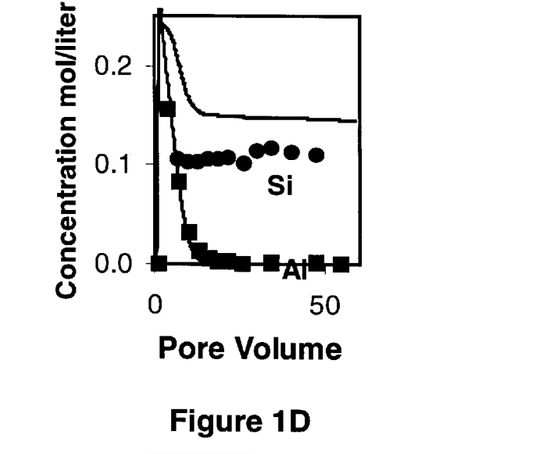
Figure 1E:
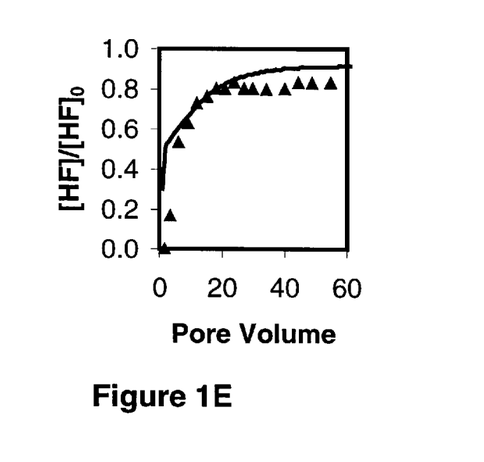
Figure 1F:
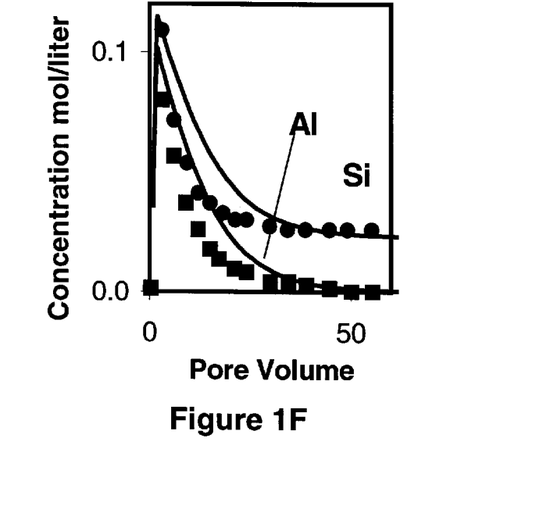
Figure 2A:
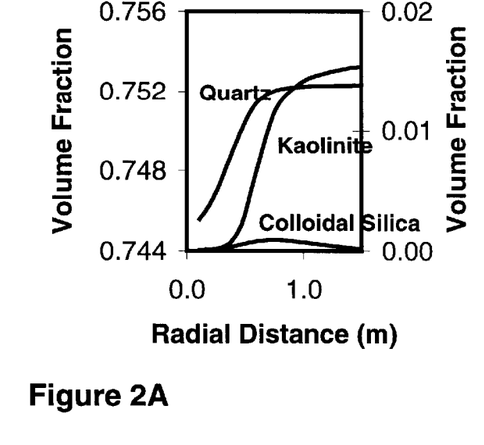
Figure 2B:
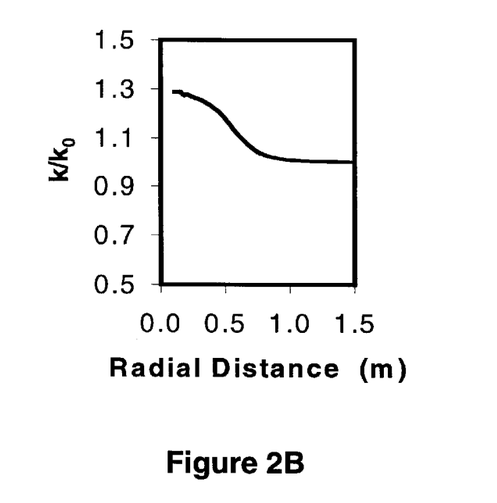
Figures 2C, 2D:
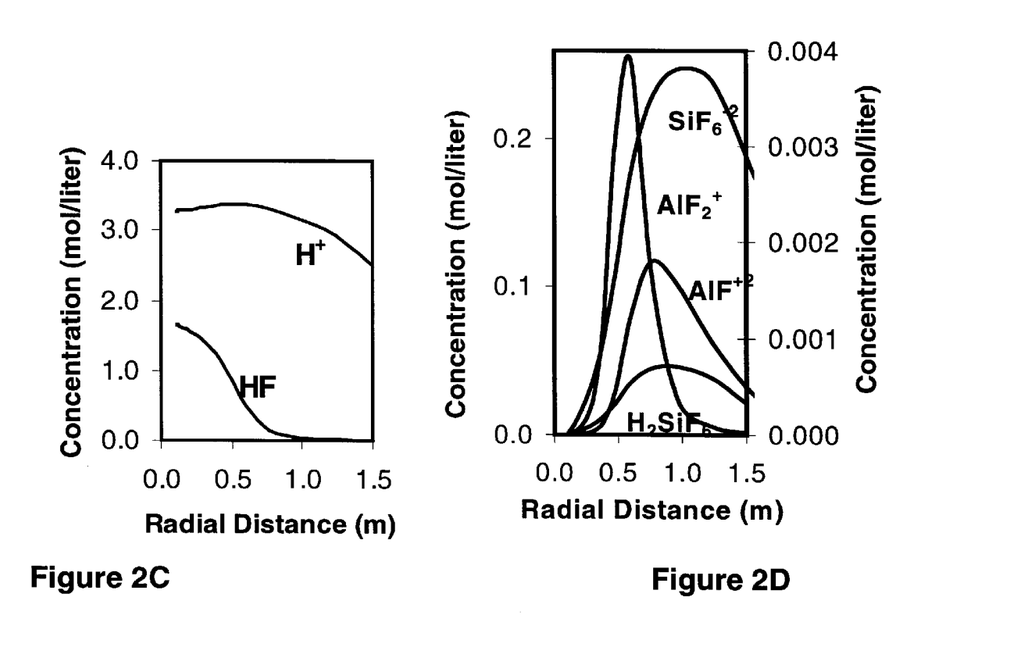

On the geochemical model is validated, it can be used to scaleup the results to the reservoir. With the present invention, this requires only a simply switch in the flow geometry from the core to reservoir flow geometry. The pay zone height was assumed to be 3.05 m (10 ft) and the wellbore diameter was assumed to be 0.2032 m (8 in). A preflush volume of 1.24 m$^3$/m (100 gal/ft) of 5 wt % HCl was used, followed by a main stage of 2.48 m$^3$/m (200 gal/ft) of 12/3 mud acid. The treatment fluids were pumped at 2.65×10$^{-3}$ m$^3$/sec (1 bbl/min). The graphs in FIG. 2 are a snapshot of the reservoir at the end of the mud acid stage. FIG. 2A shows the mineral profile in the reservoir (in FIG. 2A, the left axis is used for the quartz volume fraction and the right axis for the kaolinite and the colloidal silica). As shown in FIG. 2B, some colloidal silica precipitation did occur, but the amount was not significant enough to impact the permeability appreciably. No AlF$_3$ or Al(OH)$_4$ precipitation was observed. FIGS. 2C and 2D show the profile of the dominant aqueous species in the reservoir. HF penetration of about 0.75 m in the formation was achieved at the end of the mud acid stage. FIG. 2D shows the concentration of aluminum fluoride AlF$^{+2}$ (left axis) and AlF$_2^+$ (right axis) and the concentration of silicon fluoride SiF$_6^{2-}$ (left axis) and H$_2$SiF$_6$. This Figure shows that AlF$^{+2}$ was the dominant aluminum fluoride. Higher fluorides of aluminum than AlF$_2^+$, such as AlF$_3$, AlF$_4^-$, AlF$_5^{2-}$ and AlF$_6^{3-}$ were present in negligible concentrations. SiF$_6^{2-}$ was the dominant silicon fluoride. Other silicon fluorides were present in negligible concentrations. The aluminum and silicon species Al(OH)$^{2+}$, Al(OH)$_2^+$, Al(OH)$_4^-$, H$_3$SiO$_4^-$, H$_2$SiO$_4^{2-}$ and AlO$_2^-$ were also present in negligible concentrations.

Figure 3A:
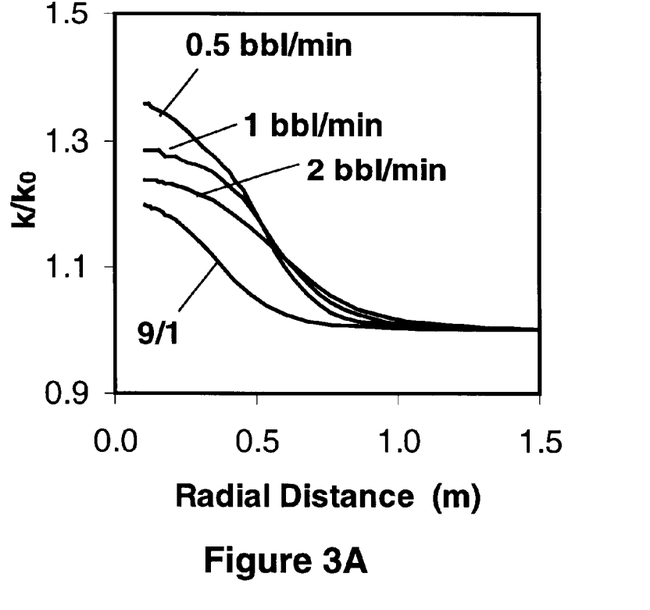
Figure 3B:
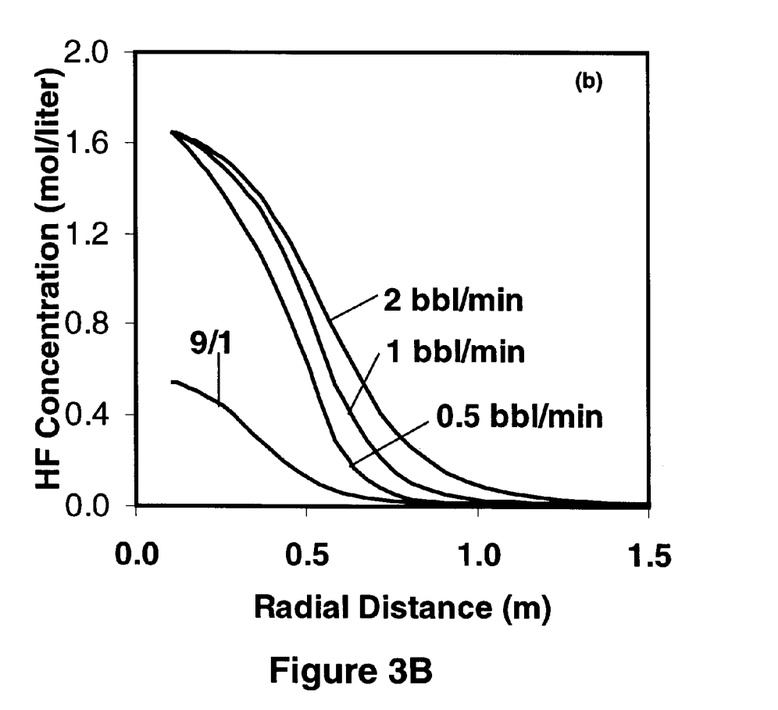

The sensitivity analysis tool facilitates optimization against any of the treatment design parameters. FIGS. 3A and 3B compare the results for the permeability (FIG. 3A) and for the HF concentration (FIG. 3B) for different injection rates and for a different mud acid formulation (9/1 mud acid) against the previous base case examined. The total injection volume was kept constant for all cases shown. At slower injection rates mineral near the sandface are preferentially dissolved, and therefore most of the permeability improvement occurs close to the wellbore. However, at extremely slow injection rates of about 0.1 bbl/min to complete shut-in (not shown), colloidal silica precipitation inhibits permeability improvement. The use of 9/1 mud acid system results in a smaller permeability improvement because the stoichiometric dissolving power of the 9/1 mud acid system is much less than that of the 12/1 mud acid system. Several variations in treatment design parameters may be similarly examined to select the optimum strategy for the final design recommendation.

Figure 4A:
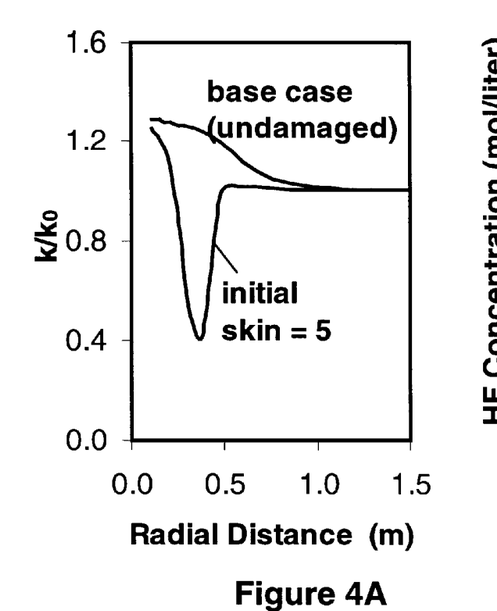
Figure 4B:
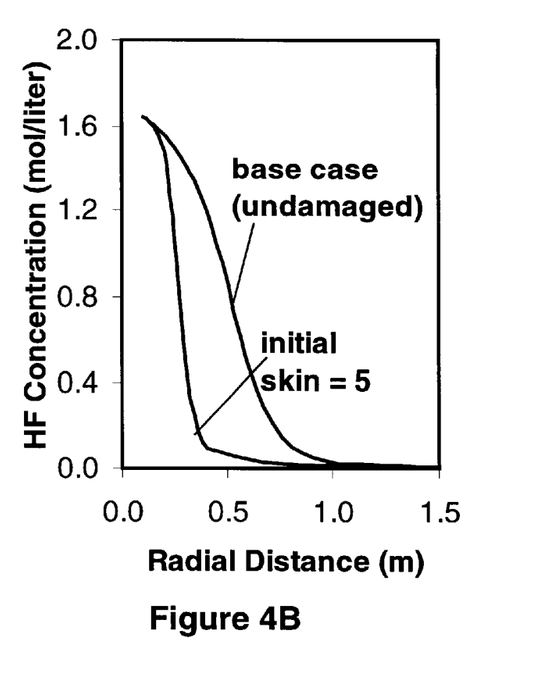
Figure 4C:
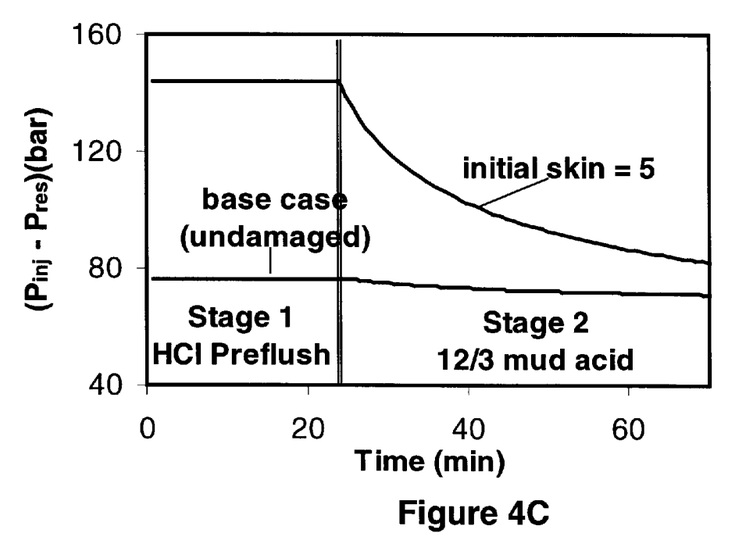

In the cases examined herein, the reservoir was considered to be undamaged initially; i.e. the skin before the treatment was zero. FIG. 4 shows the result of the treatment if the reservoir had been damaged with a mineral similar to kaolinite. More precisely, FIG. 4A shows the permeability profile, FIG. 4B the HF concentration profile and FIG. 4C the profile of the differential of pressure between the bottomhole injection pressure $P_{inj}$ and the reservoir pressure at out boundary $P_{res}$.

The damage penetration was assumed to be 0.3048 m (1 ft) and the initial skin value was assumed to be 5. All other design parameters were the same as the previous base case. If post-treatment data such as flowback analysis, post-treatment skin and injection pressure data are available, they can be compared against the predictions from the simulator, to assist in diagnosing the type, quantity and depth of damage. The information can be used to optimize future treatments for the reservoir.

While certain features and embodiments of the invention have been described in detail herein it will be understood that the invention includes all modifications and enhancements within the scope and spirit for the following claims.

What is claimed is:

1. A method for modeling a stimulation treatment for a reservoir, comprising the steps of:
   a. obtaining a set of quantified reservoir parameters including the reservoir minerals;
   b. designing a first treatment fluid comprising a mixture of chemical species;
   c. obtaining a first set of chemical reactions that can occur between the minerals and the component of the treatment fluid; said reactions defined by their equilibrium and their kinetic properties;
   d. selecting a subset of said first set of chemical reactions to create a reaction model of said minerals with said treatment fluid and predict damages consecutive of the treatment; and
   iteratively adjusting the stimulation treatment to optimize results.

2. The method of claim 1, wherein the quantified reservoir parameters include an estimate of the quantity and depth of damage to reservoir.

3. The method of claim 2, wherein the damage data includes scales.

4. The method of claim 2, wherein the damage data includes fine migration.

5. The method of claim 2, wherein the damage data are estimated from nodal analysis and mud and resistivity log data.

6. The method of claim 1, wherein the iterative step includes performing a sensitivity analysis to optimize the variables for selecting an optimum treatment design.

7. The method of claim 1, wherein the set of quantified reservoir parameters includes permeability.

8. The method of claim 7, further including a step of modeling a core test for at least one injection rate of fluid treatment, assuming a linear flow.

9. The method of claim 8, wherein the treatment includes pumping a sequence of successive fluid treatments at specific rates.

10. The method of claim 9, wherein the step of iteratively adjusting the stimulation treatment includes the step of adjusting the pumping sequence.

11. A method for modeling a stimulation treatment for a reservoir, comprising the steps of:
   a. obtaining a set of quantified reservoir parameters including the reservoir minerals, permeability and the quantity and depth of damage to the reservoir;
   b. modeling a reservoir core having a length and a diameter;
   c. designing a first treatment fluid comprising a mixture of chemical species;
   d. obtaining a first set of chemical reactions that can occur between the minerals and the component of the treatment fluid; said reactions defined by their equilibrium and their kinetic properties;
   e. selecting an injection rate of the treatment fluid;
   f. selecting a subset of said first set of chemical reactions to create a reaction model of said core with said treatment fluid and predict damages consecutive of the treatment; and
   g. iteratively adjusting the stimulation treatment to optimize results.

12. The method of claim 11, wherein the reaction model of said core assumes a linear flow of the treatment fluid along the core.

13. The method of claim 11, wherein the reaction model of said core includes effluent analysis and permeability evolution.

14. The method of claim 11, wherein said set of quantified reservoir parameters includes porosity and said reaction model includes porosity evolution.

15. A method for modeling a stimulation treatment for a reservoir, comprising the steps of:
   a. obtaining a set of quantified reservoir parameters including the reservoir minerals, permeability and the quantity and depth of damage to the reservoir;
   b. designing a first treatment fluid comprising a mixture of chemical species;
   c. obtaining a first set of chemical reactions that can occur between the minerals and the component of the treatment fluid; said reactions defined by their equilibrium and their kinetic properties;
   d. selecting an injection rate of the treatment fluid;
   e. selecting a subset of said first set of chemical reactions to create a reaction model of said reservoir with said treatment fluid and predict damages consecutive of the treatment; and
   f. iteratively adjusting the stimulation treatment to optimize results.

16. The method of claim 14, wherein the damage data are estimated from nodal analysis and mud and resistivity log data.

17. The method of claim 14, wherein the iterative step includes performing a sensitivity analysis to optimize the variables for selecting an optimum treatment design.

18. The method of claim 14, wherein the reaction model assumes a radial flow of the treatment fluid.

19. The method of claim 14, wherein the reaction model of said reservoir includes effluent analysis and permeability evolution.

20. The method of claim 14, wherein the thermodynamic data for the chemical species is calculated from the following thermodynamic identity:

$$\ln(K) = \frac{-\sum v_i \mu_i^o}{RT}$$

where K is the equilibrium constant, $v_i$ the stoechiometric coefficient of species i, $\mu_i^o$, the standard chemical potential of species i, R the gas constant and T the temperature.

21. The method of claim 20 wherein once the standard chemical potential $\mu_i^o$ (T,P) for the aqueous species i is computed at stimulation temperature and pressure, the chemical potential of the aqueous species in solution $\mu_i$(T, P, $\vec{m}$) is then computed internally in the simulator from the following equation:

$$\mu_i(T, P, \vec{m}) = \mu_i^o(T, P) + RT \ln \gamma_i(T, P, \vec{m}) m_i$$

where $\gamma_i$ is the activity coefficient for species i, at temperature T, pressure P and molality mi.

22. A method for performing a stimulation treatment for a reservoir, comprising the steps of:
   a. obtaining a set of quantified reservoir parameters including the reservoir minerals, permeability and the quantity and depth of damage to the reservoir;
   b. designing a first treatment fluid comprising a mixture of chemical species;
   c. obtaining a first set of chemical reactions that can occur between the minerals and the component of the treatment fluid; said reactions defined by their equilibrium and their kinetic properties and therefore creating a mathematical model of the treatment;
   d. selecting an injection rate of the first treatment fluid;
   e. selecting a subset of said first set of chemical reactions to create a reaction model of said reservoir with said treatment fluid and predict damages consecutive of the treatment;
   f. pumping said first treatment fluid at a first injection rate while measuring the bottomhole pressure;
   g. computing real-time damages to the reservoir from the measured bottomhole pressure and injection rate;
   h. simultaneously computing the damages based on the mathematical model; and
   g. adjusting the stimulation treatment to optimize results.

23. A method for designing a stimulation treatment fluid for a reservoir, comprising the steps of:
   a. obtaining a set of quantified reservoir parameters including the reservoir minerals;
   b. designing a first treatment fluid comprising a mixture of chemical species;
   c. obtaining a first set of chemical reactions that can occur between the minerals and the component of the treat ment fluid; said reactions defined by their equilibrium and their kinetic properties and therefore creating a mathematical model of the treatment;

d. selecting a subset of said first set of chemical reactions to create a reaction model of said reservoir minerals with said treatment fluid and predict damages consecutive of the treatment;

e. iteratively adjusting the stimulation treatment to optimize results; and f. performing laboratory experiments on the optimized stimulation treatments thereby reducing the number of experiments required for designing a new treatment.

* * * * *